United States Patent [19]
Weddendorf

[11] Patent Number: 5,314,500
[45] Date of Patent: May 24, 1994

[54] PROSTHETIC ELBOW JOINT

[75] Inventor: Bruce C. Weddendorf, Decatur, Ala.

[73] Assignee: The United States of America as represented by the Administrator, National Aeronautics and Space Administration, Washington, D.C.

[21] Appl. No.: 912,953

[22] Filed: Jul. 8, 1992

[51] Int. Cl.$^5$ .......................... A61F 2/66; A61F 2/54; A61F 2/58
[52] U.S. Cl. ........................................ 623/57; 623/59; 623/60
[58] Field of Search .................. 623/63, 57, 59, 60

[56] References Cited

U.S. PATENT DOCUMENTS

| | | | |
|---|---|---|---|
| 1,346,092 | 7/1920 | Hullinger | 623/59 |
| 1,469,431 | 10/1923 | Arnal | 623/59 |
| 4,636,221 | 1/1987 | Kemp | 623/59 |

OTHER PUBLICATIONS

Durability and Reliability of Externally Powered Elbow Protheses, Dated Apr. 25, 1991, National Easter Seal Society.

*Primary Examiner*—Randall L. Green
*Assistant Examiner*—Dinh X. Nguyen
*Attorney, Agent, or Firm*—Robert L. Broad, Jr.; Guy M. Miller; John R. Manning

[57] ABSTRACT

An artificial manually positionable elbow joint for use in an upper extremity, above-elbow, prosthetic which provides a locking feature that is easily controlled by the wearer. The instant elbow joint is very strong and durable to withstand the repeated heavy loadings encountered by a wearer who works in an industrial, construction, farming or similar environment. The elbow joint of the present invention comprises a turntable, a frame, a forearm and a locking assembly. The frame generally includes a housing for the locking assembly and two protruding ears. The forearm includes an elongated beam having a cup-shaped cylindrical member at one end and a locking wheel having a plurality of holes along a circular arc on its other end with a central bore for pivotal attachment to the protruding ears of the frame. The locking assembly includes a collar having a central opening with a plurality of internal grooves, a plurality of internal cam members each having a chamfered surface at one end and a V-shaped slot at its other end; an elongated locking pin having a crown wheel with cam surfaces and locking lugs secured thereto; two coiled compression springs; and a flexible filament attached to one end of the elongated locking pin and extending from the locking assembly for extending and retracting the locking pin into the holes in the locking wheel to permit selective adjustment of the forearm relative to the frame. In use, the turntable is affixed to the upper arm part of the prosthetic (not shown) in the conventional manner and the cup-shaped cylindrical member on one end of the forearm is affixed to the forearm piece of the prosthetic (not shown) in the conventional manner. The elbow joint is easily adjusted and locked between maximum flex and extended positions.

14 Claims, 4 Drawing Sheets

PROSTHETIC ELBOW JOINT

ORIGIN OF THE INVENTION

The invention described herein was made by an employee of the United States Government and may be manufactured and used by or for the Government for governmental purposes without the payment of any royalties thereon or therefor.

FIELD OF THE INVENTION

The present invention relates generally to a prosthetic elbow joint. More particularly, this invention relates to an artificial manually positionable elbow joint for use in an upper extremity, above-elbow, prosthetic which provides a locking feature that is controlled by the wearer.

BACKGROUND OF THE INVENTION

The prior art includes numerous prosthetic elbow joints to be worn by persons who were either born with no elbow, forearm and hand or whose arm had been amputated in the upper arm above the elbow. Most of the prior art prosthetic elbow joints generally include a turntable for affixing to the upper arm part of the prosthesis, a pivotal elbow joint, and a forearm. The most prominently used prosthetic elbow joint appears to be Models Numbered E-400 and E-400HD made and sold by Hosmer Dorrance Corporation, Campbell, Calif., as described in its catalogs, 10th edition (copyright 1983) and 11th edition (copyright 1986). These prior art prosthetic elbow joints have three major drawbacks or disadvantages. The first drawback or disadvantage of these prior art elbow joints reside in the fact that their extremely complex and fragile structure are not only costly to manufacture and sell, but the joints often fail when subjected to heavy use by many of its wearers. The second drawback or disadvantage relates to the extreme complexity of these devices and their numerous parts which make the elbow joints very difficult to disassemble, requiring the use of several different tools, a particularly difficult task for a person with only one hand. A third drawback or disadvantage of these prior art prosthetic elbow joints resides in their appearance in that the forearm part of the prosthesis is affixed to the elbow by an external steel fork which is exposed on the outside of the prosthesis. While a flesh colored plastic cap covers the mechanisms, the cap is hidden in part by the large steel fork which straddles the cap to give an overall, unnatural, appearance.

The present invention overcomes the several disadvantages, drawbacks or deficiencies of the prior art devices in that it provides a very strong joint which can withstand the repeated heavy loading encountered by a wearer who works in an industrial, construction, farming or similar environments. The strength of the present invention is due to the locking method utilized, a pin through a locking wheel loaded in double shear. The present invention is also very simple, having fewer parts, being less expensive to manufacture, and designed to be easily and quickly disassembled by a person with only one hand by use of only a screwdriver, penknife or other simple tool. The present invention also has the advantage of being fully covered by a single, flesh colored, rubber sleeve to give a more natural appearance.

Accordingly, it is an object of the present invention to provide a prosthetic elbow joint which is simple in construction, inexpensive to manufacture, and which incorporates locking features that can withstand repeated heavy loadings.

It is still a further object of the present invention to provide a prosthetic elbow joint which is simple in construction, inexpensive to manufacture, pleasing in appearance, and adapted to be easily locked and unlocked in several different positions.

Other aspects, objects and advantages of this invention will become apparent to those skilled in the art to which this invention pertains from a study of the preferred embodiment as set forth in the specification, drawings and appended claims.

DESCRIPTION OF THE PREFERRED EMBODIMENT

Figure 1:
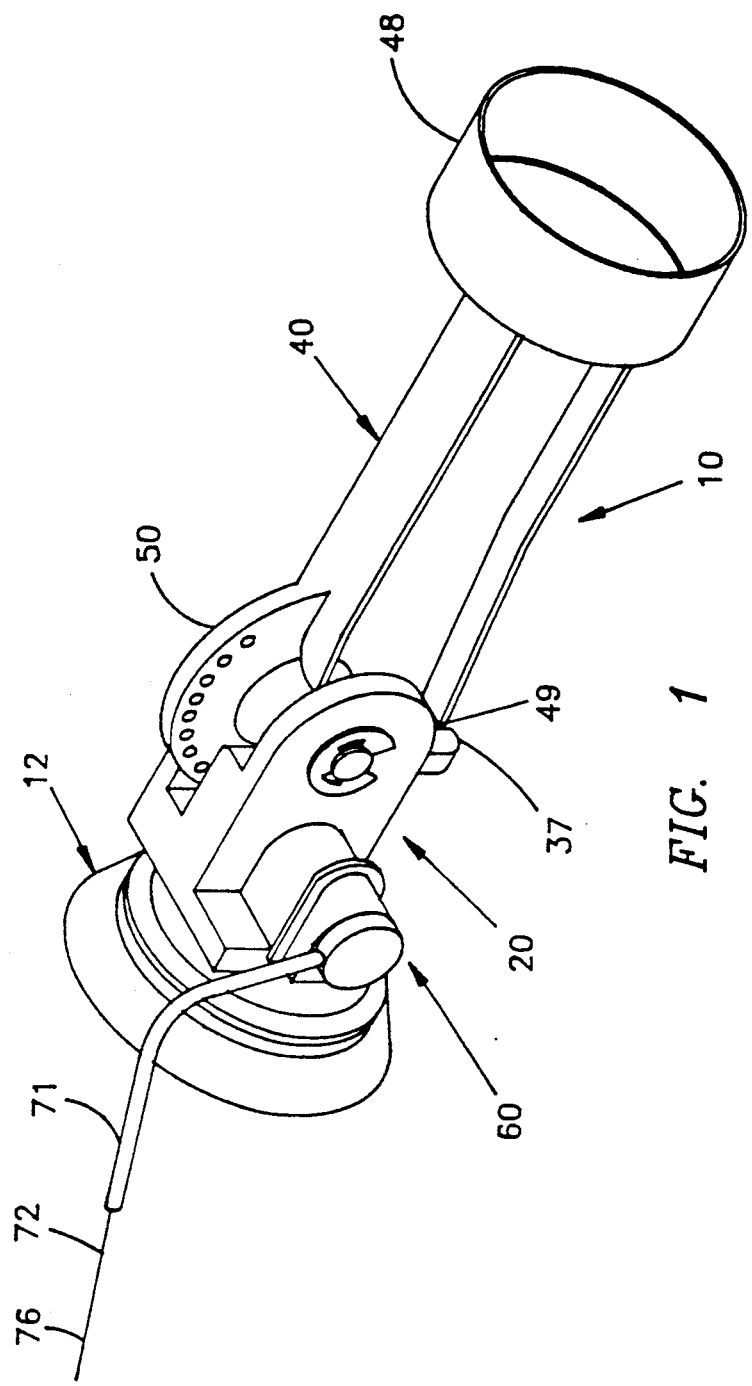
FIG. 1 is a perspective view of an assembled prosthetic elbow joint of the present invention.

Referring now to the drawings, reference numeral 10 designates the prosthetic elbow joint of the present invention. Prosthetic elbow joint 10 is best illustrated in its assembled condition in FIG. 1 and in its nonassembled or exploded condition in FIG. 2. As best shown in FIG. 1, prosthetic elbow joint 10 generally comprises a turntable 12, a frame 20, a forearm 40, and a locking assembly or mechanism 60.

Figure 2:
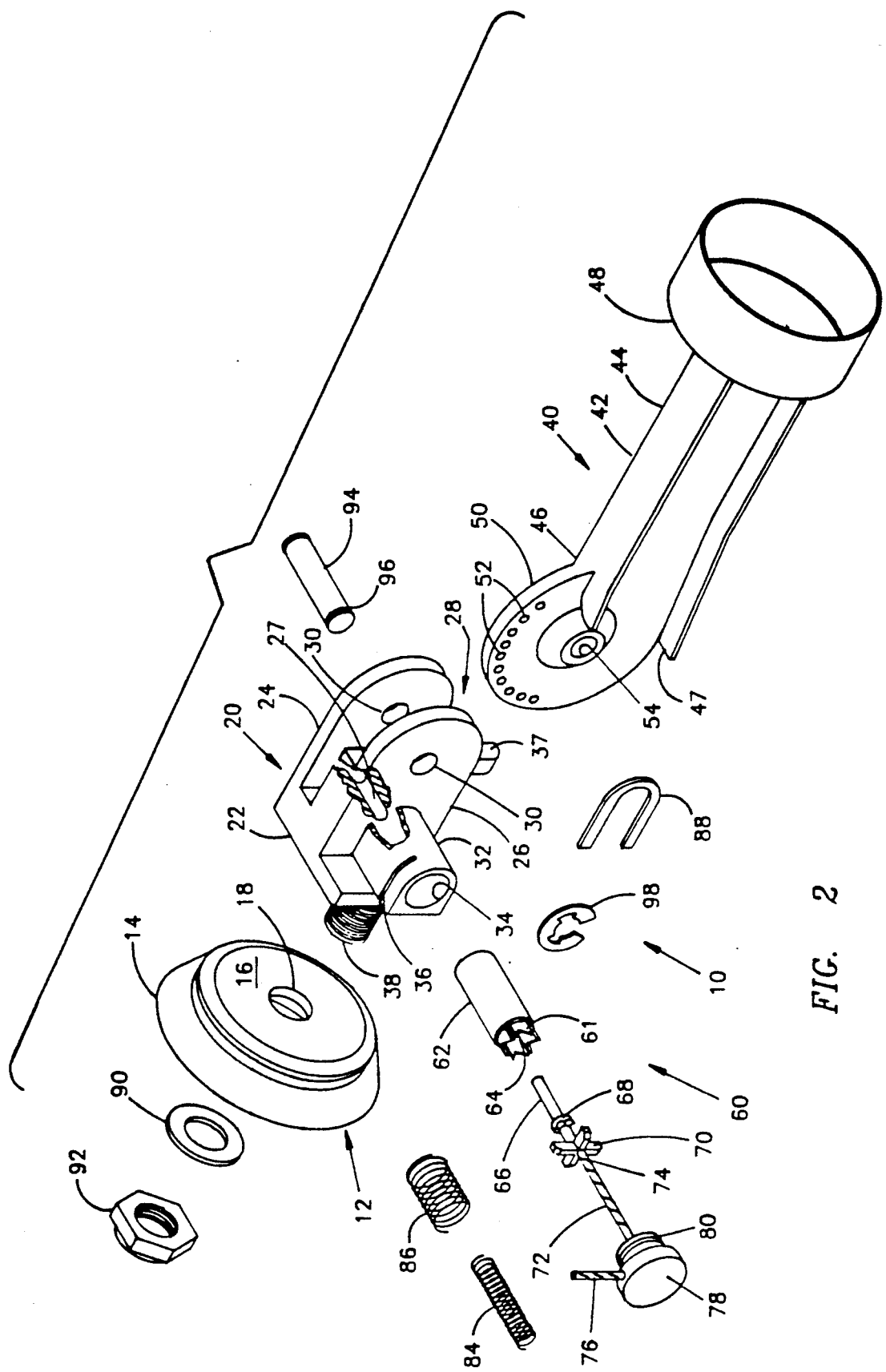
FIG. 2 is an exploded, partially broken away, perspective, view of the prosthetic elbow joint of the present invention.

As best illustrated in FIG. 2, turntable 12 is hollow and cup-shaped having a cylindrical wall 14 and a bottom 16 with a central round opening 18. Also as best illustrated in FIG. 2, frame 20 includes a base 22, first and second ears 24 and 26 secured thereto and extending therefrom separated by a stepped-up recess 28, a bore 30 through each of first and second ears 24 and 26, a housing 32 extending outwardly from second ear 26 and having a circular bore 34 and two spaced diametrically opposed grooves 36 which extend within circular bore 34, stop member 37 secured to and extending from second ear 26, a bore 27 through ear 26 and in communication with bore 34 of housing 32, and a threaded stud 38 secured to and extending from base 22.

As also best illustrated in FIG. 2, forearm 40 includes a beam 42 having a first end 44 and a second end 46, a hollow, cup-shaped, cylindrical member 48 on first end 44, a generally round locking wheel 50 on second end 46 of beam 42 having a plurality of spaced holes 52 therein along a circular arc on its outer perimeter, a stop member 47 on second end 46 of beam 42, and a circular bore 54 extending through locking wheel 50.

Figure 3:
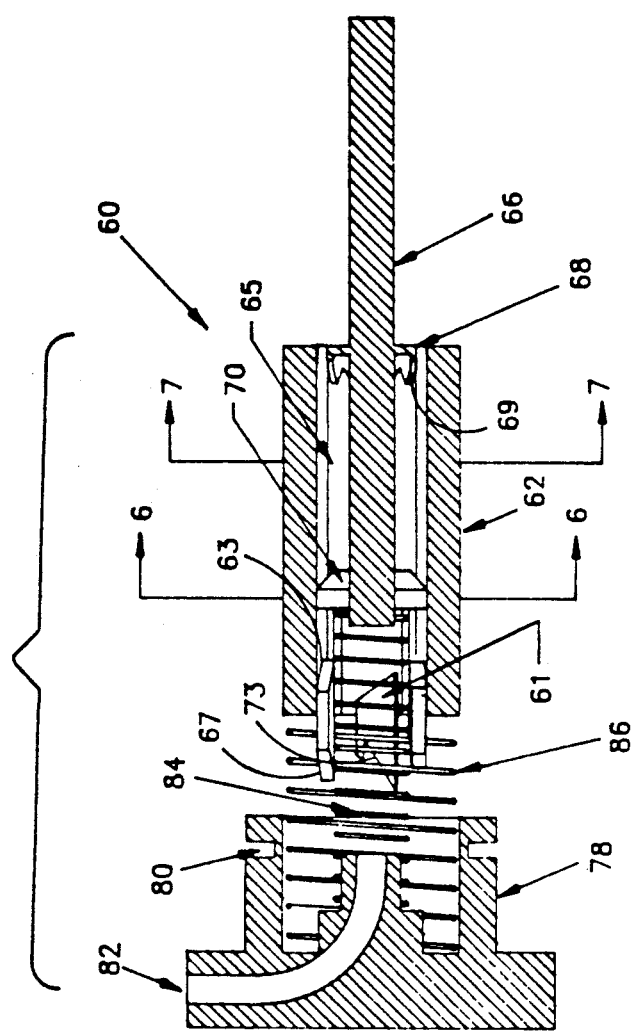
FIG. 3 is an exploded cross sectional view showing details of the locking assembly of the prosthetic elbow joint of the present invention.
Figure 7:
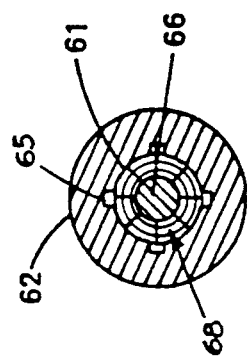
FIG. 7 is a sectional view taken along line 7—7 of FIG. 3.
Figure 6:
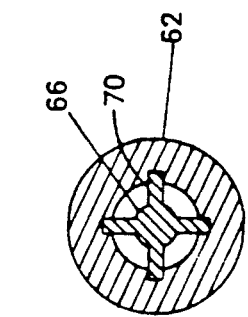
FIG. 6 is a sectional view taken along line 6—6 of FIG. 3.

As best illustrated in FIGS. 2, 3, 6 and 7 locking assembly 60 includes a cylindrical, hollow, collar 62 having a central opening 64 with a plurality of internal grooves 65 (FIGS. 5 and 7) therethrough, a plurality of internal cam members 61, each cam member 61 having a first chamfered surface 63 at one end and a second chamfered surface 67 at its other end with each second chamfered surface 67 including a generally V-shaped slot 73 (FIG. 3) therein, a round, elongated, locking pin 66 having a crown wheel 68, with a plurality of generally V-shaped cam surfaces 69 thereon, and a plurality of lugs 70 affixed thereto, each of the lugs 70 being adapted for sliding movement within one of said internal grooves 65 of opening 64 of collar 62 (FIG. 6) and the crown wheel 68 being adapted for sliding movement within opening 64 of collar 62 (FIG. 7), a flexible sheathing 71 (FIG. 1), a control wire 72 slidably mounted within sheathing 71 and having a first end 74 secured to locking pin 66 adjacent lugs 70 and a second end 76, a plug 78 having an external groove 80 and an internal curved passageway 82 (FIG. 3) for receiving the control wire 72 and allowing its second end 76 to protrude therefrom, a first compression coil spring 84 mounted within collar 62 for acting on lugs 70 and plug 78 to normally urge locking pin 66 to its extended, locking, position as shown in FIG. 3, a second compression coiled spring 86 mounted partially over cam members 61 of collar 62 for acting on collar 62 and plug 78 to normally urge collar 62 into the bore 34 of housing 32 so that the inner edge of collar 62 seats against a shoulder formed on second ear 26 in an area surrounding the bore 27 in second ear 26 through which pin 66 penetrates before and after its entry into a selected hole 52 in locking wheel 50, and a C-shaped clip 88 for passing through the two diametrically opposed grooves 36 of housing 32 and groove 80 of plug 78 to secure the locking mechanism 60 to frame 20.

Frame 20, with locking assembly or mechanism 60 mounted and secured within housing 32, is secured to cup-shaped turntable 12 by passing threaded stud 38 through central opening 18 of turntable 12, applying washer 90 and threaded nut 92 over threaded stud 38, and tightening nut 92 on threaded stud 38. Forearm 40 is secured to frame 20 by passing pin 94 having circular groove 96 adjacent one end through bore 30 of first ear 24, bore 54 of locking wheel 50, and bore 30 of second ear 26 and applying a second C-shaped clip 98 in groove 96 of pin 94. A flesh colored elastic sleeve (not shown) can be placed over prosthetic elbow joint 10 to tightly engage the cylindrical wall 14 of turntable 12 and the outer wall of hollow, cup-shaped, cylindrical member 48 to cover the prosthetic elbow joint 10 to hide it and provide a more natural appearance.

Figure 4:
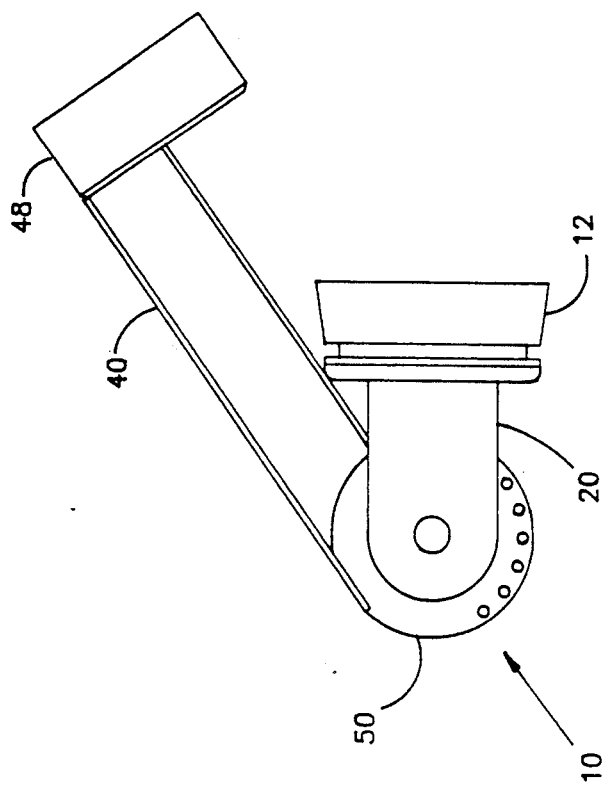
FIG. 4 is a side view of the prosthetic elbow joint of the present invention depicted in its maximum flexed condition.
Figure 5:
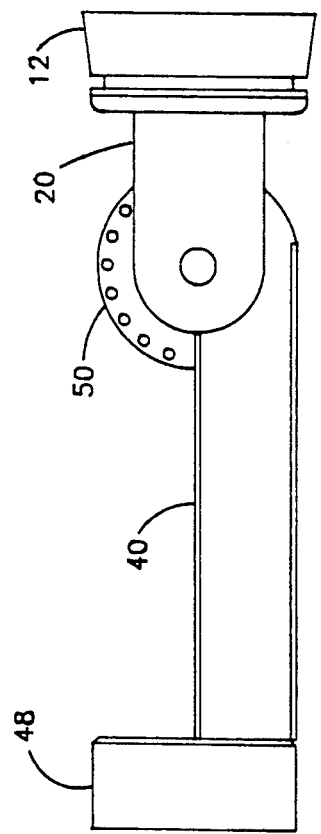
FIG. 5 is a side view of the prosthetic elbow joint of the present invention depicted in its maximum extended condition.

FIGS. 4 and 5 show the prosthetic elbow joint 10 in its two extreme positions. FIG. 4 illustrates prosthetic elbow joint 10 in its maximum flex position and FIG. 5 illustrates prosthetic elbow joint 10 in its maximum extended position.

In operation, turntable 12 is affixed to the upper arm part of the prosthesis (not shown) in the conventional manner after first loosening and then tightening nut 92 to allow rotational alignment of elbow joint 10 to the upper arm prosthesis. The cup-shaped cylindrical member 48 of beam 42 is then attached to the forearm piece (not shown) of the prosthesis (not shown) in the usual manner. Assuming that, upon mounting of elbow joint 10 on the upper arm and forearm parts of the prosthesis, the elbow joint 10 is locked in its fully extended position as shown in FIG. 5 with the stop member 47 on beam 42 engaging stop member 37 of frame 20 and locking pin 66 being in engagement with the surface surrounding an end hole 52 in locking wheel 50, the wearer of elbow joint 10 will pull on control wire 72 thereby removing locking pin 66, against the force of compression spring 84, from the end hole 52 of locking wheel 50 and lugs 70 from the internal grooves 65 in central opening 64 of collar 62 to a position beyond second chamfered surfaces 67 of the cam members 61 at which time generally V-shaped cam surfaces 69 of crown wheel 68 engage first chamfered surfaces 63 of cam members 61 to cause collar 62 to rotate $\frac{1}{8}$ revolution and upon the release of control wire 72 compression spring 84 urges lugs 70 into V-shaped slots 73 of second chamfered surfaces 67 of cam members 61 which hold locking pin 66 in its retracted, unlocked, position. The forearm 40 is then rotated about bore 54 to a desired flex position where locking pin 66 will be in alignment with another hole 52 in locking wheel 50 and the control wire 72 will then be pulled to cause the V-shaped cam surfaces 69 of crown wheel 68 to engage the first chamfered surfaces 63 of cam members 61 to again rotate collar 62 $\frac{1}{8}$ revolution and thus free lugs 70 of locking pin 66 from V-shaped slots 73 of second chamfered surfaces 67 of cam members 61 so that first compression coil spring 84 forces locking pin 66 into the hole 52 of locking wheel 50 in alignment therewith to thus lock forearm 40 in such position. When the control wire 72 is next pulled, the pin 66 will be removed from a hole 52 of locking wheel 50 and the lugs 70 will be in a position behind second chamfered surfaces 67 at which time the V-shaped cam surfaces 69 of crown wheel 68 engage the first chamfered surfaces 63 of collar 62 to rotate collar 62 $\frac{1}{8}$ revolution and upon the release of control wire 72, compression spring 84 urges lugs 70 into V-shaped slots 73 of second chamfered surfaces 67 of cam members 61 to again hold pin 66 in its retracted, unlocked, position. The forearm 40 is then rotated about bore 54 to a desired flex position where locking pin 66 will be in alignment with another hole in locking wheel 50 and the control wire 72 will again be pulled to free lugs 70 from V-shaped slot 73 to allow the lugs 70 to slide within internal grooves 65 of collar 62 and thereby allow locking pin 66 to be forced by compression spring 84 to enter a hole 52 to lock the joint 10 in the desired positions.

This procedure is continued each time that the wearer desires to place elbow joint 10 into a new position. In practice, each pull on control wire 72 will alternately extend or retract pin 66 from its locking and unlocking positions. With each adjustment of elbow joint 10 to a new position, the collar 62 is forced to move a short distance longitudinally, against the force of second coiled spring 86, by contact of first chamfered surfaces 63 with cam surfaces 69 of crown wheel 68, which force causes the V-shaped cam surfaces 69 of crown wheel 68 to slide along the chamfered surfaces 63 of cam members 61 thereby forcing each $\frac{1}{8}$th revolution of collar 62.

While the above description constitutes a preferred embodiment of the present invention, it will be appreciated that the invention is susceptible to modification, variation and change without departing from the proper scope and fair meaning of the accompanying claims.

I claim:

1. A manually positionable elbow joint for attachment to and between an upper extremity, above-elbow, prosthetic and a forearm prosthetic, said elbow joint comprising:

a turntable for attachment to said upper extremity, above-elbow prosthetic;

a frame secured to said turntable, said frame having a base;

a forearm including an elongated beam having first and second ends, means on said second end of said beam for pivotal attachment to said frame including a generally round locking wheel having a central bore therein, at least one bore in said frame and means for passing through said bores for securing said forearm to said frame including a pin having first and second ends, an enlarged shoulder at said first end and a circular groove having opposed walls at said second end, and a C-clip for frictional engagement with said walls of said circular groove, and means on said first end of said beam for attachment to said forearm prosthetic;

a housing secured to said frame; and forearm locking means carried in said housing and including a member for reciprocal movement therein into and out of engagement with said means on said second end of said forearm for selectively locking said forearm in a plurality of positions between maximum extended and flexed conditions.

2. The manually positionable elbow joint of claim 1 wherein said means on said first end of said beam for attachment to said forearm prosthetic includes a hollow, cup-shaped member.

3. The manually positionable elbow joint of claim 2 wherein said generally round locking wheel of said forearm includes an outer perimeter and a plurality of spaced holes in said outer perimeter along a circular arc.

4. The manually positionable elbow joint of claim 3 wherein said forearm locking means carried in said housing for selectively locking said forearm in a plurality of positions comprises a collar having a central opening and a plurality of cam members at one end thereof, a pin slidably mounted within said central opening for movement between extended, locking, and retracted, unlocking, positions, a plurality of lugs mounted on said pin, and a compression spring for acting on said lugs for normally urging said pin into said locking position.

5. The manually positionable elbow joint of claim 4 wherein said forearm locking means further includes an end plug having a curved passageway therein and a flexible filament extending through and projecting from said passageway and being secured to said pin at one end thereof.

6. The manually positionable elbow joint of claim 5 wherein each of said cam members include first and second chamfered surfaces, each of said second chamfered surfaces including a slot therein for engaging said lugs for holding said pin in its said retracted, unlocking, position.

7. A manually positionable elbow joint for attachment to and between an upper extremity, above-elbow, prosthetic and a forearm prosthetic, said elbow joint comprising:

a turntable for attachment to said upper extremity, above-elbow, prosthetic;

a frame having a base, a lower portion extending from said base, and a housing extending from said lower portion and having a bore therein, said lower portion and housing defining a recess therebetween;

a forearm including an elongated beam having first and second ends, means on said second end of said beam for pivotal attachment to said lower portion of said frame within said recess between said lower portion and said housing of said frame including a generally round locking wheel having a central bore therein, at least one bore in said lower portion of said frame and means for passing through said bores for securing said forearm to said frame including a pin having first and second ends, an enlarged shoulder on said first end and a circular groove in said second end, and a C-clip for frictional engagement with the walls of said circular groove, and means on said first end of said beam for attachment to said forearm prosthetic; and means partially positioned within said bore of said housing of said frame for engaging said means on said second end of said forearm for selectively locking said forearm in a plurality of positions between maximum extended and flexed conditions.

8. The manually positionable elbow joint of claim 7 wherein said means on said first end of said beam for attachment to said forearm prosthetic includes a hollow, cup-shaped member.

9. The manually positionable elbow joint of claim 8 wherein said generally round locking wheel of said forearm includes a plurality of spaced holes therein along a circular arc on its outer perimeter.

10. The manually positionable elbow joint of claim 9 wherein said means partially positioned within said bore of said housing of said frame for selectively locking said forearm in a plurality of positions comprises a collar having a central opening and a plurality of cam members at one end thereof, a pin slidably mounted within said central opening for movement between extended, locking, and retracted, unlocking, positions, a plurality of lugs mounted on said pin, and a compression spring for acting on said lugs for normally urging said pin into said locking position.

11. The manually positionable elbow joint of claim 10 wherein said means for selectively locking said forearm in a plurality of positions further includes an end plug having a curved passageway therein and a flexible filament extending through and projecting from said passageway and being secured to said pin at one end thereof.

12. The manually positionable elbow joint of claim 11 wherein each of said cam members include first and second chamfered surfaces, each of said second chamfered surfaces including a slot therein for engaging said lugs for holding said pin in its retracted, unlocking, position.

13. An artificial manually positionable elbow joint for attachment to and between an upper extremity, above-elbow, prosthetic and a forearm prosthetic, said elbow joint comprising:

a turntable for attachment to said upper extremity, above-elbow, prosthetic;

a frame having a base, first and second ears extending from said base and defining a recess therebetween, a first bore in each of said first and second ears, a second bore in said first ear, and a stud extending from said base and being adjustably secured to said turntable;

a housing secured to said first ear of said frame, said housing including a central bore in alignment with said second bore of said first ear of said frame, said central bore in said housing being of greater diameter than said second bore of said first ear;

a forearm including an elongated beam having first and second end portions, a generally round locking wheel fixed to said first end portion, said locking wheel including a central bore an outer perimeter and a plurality of spaced holes having walls along a circular arc adjacent said outer perimeter, said locking wheel being pivotally secured to said first and second ears of said frame within said recess, and means on said second end portion of said beam for attachment to said forearm prosthetic;

forearm locking means partially positioned within said central bore of said housing for engaging said walls of a selected said hole adjacent the outer perimeter of said locking wheel for selectively locking and unlocking said forearm in a plurality of positions between maximum extended and flexed conditions; and means for actuating said forearm locking means to cause said locking and unlocking of said forearm.

14. The artificial manually positionable elbow joint of claim 13 wherein said forearm locking means comprises a collar having a central opening and first and second ends, a plurality of longitudinal grooves within said central opening, and a plurality of cam members secured to said first end, each of said cam members having an inner end and an outer end, a chamfered surface on said inner end of each said cam member and a V-shaped slot in said outer end of each said cam member; and a pin including a plurality of radially extending lugs, a crown wheel having a plurality of cam surfaces thereon, said pin being slidably mounted within said central opening of said collar with each of said lugs being selectively engaged with the walls of a respective said groove of said collar; and a compression spring for acting on said lugs for normally urging said pin toward its said locking position, said cam surfaces on said crown wheel being adapted for engaging said chamfered surfaces of said cam members to cause rotation of said collar for causing said lugs to be engaged and disengaged in said V-shaped slot in said outer end of said cam members.

* * * * *